United States Patent
Guday et al.

(10) Patent No.: US 7,292,956 B1
(45) Date of Patent: Nov. 6, 2007

(54) FEDERATED SENSING, ANALYSIS, SUMMARIZATION, AND SHARING OF DATA FOR HEALTHCARE

(75) Inventors: Shai Guday, Redmond, WA (US); Ruston John David Panabaker, Bellevue, WA (US); Eric Horvitz, Kirkland, WA (US); Michael Sinclair, Kirkland, WA (US); William Jefferson Westerinen, Issaquah, WA (US); Feng Zhao, Issaquah, WA (US)

(73) Assignee: Microsoft Corporation, Redmond, WA (US)

( * ) Notice: Subject to any disclaimer, the term of this patent is extended or adjusted under 35 U.S.C. 154(b) by 0 days.

(21) Appl. No.: 11/561,855

(22) Filed: Nov. 20, 2006

(51) Int. Cl.
*G06F 3/01* (2006.01)
(52) U.S. Cl. .................. 702/118; 702/120; 702/122; 702/126
(58) Field of Classification Search ............... 702/19, 702/20, 118, 176, 182, 185, 120, 122, 126; 340/573.1; 356/73; 600/300; 700/29
See application file for complete search history.

(56) References Cited

U.S. PATENT DOCUMENTS

| | | | |
|---|---|---|---|
| 5,713,350 A | 2/1998 | Yokota et al. | |
| 6,053,887 A | 4/2000 | Levitas et al. | |
| 6,398,727 B1 | 6/2002 | Bui et al. | |
| 6,551,243 B2 | 4/2003 | Bocionek et al. | |
| 7,130,678 B2 * | 10/2006 | Ritscher et al. | 600/523 |
| 7,212,128 B2 * | 5/2007 | Schenker | 340/573.1 |
| 2004/0133081 A1 * | 7/2004 | Teller et al. | 600/300 |
| 2004/0260155 A1 | 12/2004 | Ciamiello et al. | |
| 2005/0138017 A1 | 6/2005 | Keen et al. | |
| 2005/0192845 A1 | 9/2005 | Brinsfield et al. | |
| 2006/0173713 A1 | 8/2006 | Petro et al. | |
| 2006/0173715 A1 | 8/2006 | Wang | |
| 2006/0253045 A1 * | 11/2006 | Coifman | 600/538 |

FOREIGN PATENT DOCUMENTS

WO    WO 2006/006176 A3    1/2006

OTHER PUBLICATIONS

Bruce W. Bode et al. "Using the Continuous Glucose Monitoring System to Improve the Management of Type 1 Diabetes", Diabetes Technology and Therapeutics, vol. 2, Supplement 1, 2000, Mary Ann Liebert, Inc.

(Continued)

*Primary Examiner*—Eliseo Ramos-Feliciano
*Assistant Examiner*—Felix Suarez

(57) ABSTRACT

A method and system is provided for management of medical data from a network of devices. The network of devices may include federated sensors that collect and forward medical data pertaining to an individual or biological specimen. The federated sensors or a central or remote device may further process the medical data and assign a priority value to the medical data. Processing can also include the analysis of the data for sensor error, local fusion of multiple sensors into higher-level interpretations, and the summarization or abstraction of the data into information that people are more comfortable with sharing than they might be with transmittal of the base data. The medical data may be transported to a healthcare provider or other endpoints based on the priority value and the authorization of recipient.

22 Claims, 10 Drawing Sheets

OTHER PUBLICATIONS

Benjamin Jung et al. "SynExML as a vehicle for Electronic Patient Records", A status report from the SynEx project, 2000.

Body Sensor Networks. BSN 2006, International Workshop on Wearable and Implantable Body Sensor Networks, Apr. 3-5, 2006 at MIT.

Irfan A. Essa "Ubiquitous Sensing for Smart and Aware Environments: Technologies towards the building of an Aware Home", IEEE Personal Communications, Oct. 2000.

William Grimson et al. "Federated Healthcare Record Server—the Synapses Paradigm", International journal of medical informatics, 1998.

Wilhelm Hasselbring "Federated Integration of Replicated Information Within hospitals", International Journal on Digital Libraries, 1997.

Loren Schwiebert et al. "Research Challenges in Wireless Networks of Biomedical Sensors", ACM Sigmobile, 2001.

Anind K. Dey et al. "A Context-Based Infrastructure for Smart Environments", Proceedings of the 1st International Workshop on Managing Interactions in Smart Environments (MANSE '99), 1999.

Victor Shnayder et al. "Sensor Networks for Medical Care", Technical Report TR-08-05, Division of Engineering and Applied Sciences, Harvard University, 2005.

Bryan L. Gorman et al. "Advancing Sensor Web Interoperability", Apr. 1, 2005.

* cited by examiner

FEDERATED SENSING, ANALYSIS, SUMMARIZATION, AND SHARING OF DATA FOR HEALTHCARE

BACKGROUND

A sensor device for sensing biological or clinical data may communicate data with other similar sensor devices. Such data may be used for management of healthcare. However, several challenges exist for the collection, fusion, interpretation, and sharing of the data with appropriate privacy and security. There can be a great deal of information from such networks and thus, healthcare providers, such as physicians or nurses, may become overwhelmed by the volume of data received. In addition, data from patients may not have an adequate level of reliability. For example, if data is improperly collected, the data may be corrupted or inaccurate. Also, patient data may be sensitive such that it may be desired that certain types of data be kept private. These problems may be encountered in non-healthcare settings as well such as in any situation in which large amounts of information can overwhelm a user.

Often only certain portions of the voluminous information received pertains to a critical condition or event in which action must be taken immediately. In a healthcare setting, other portions of the data may describe only routine conditions in which care need not be administered on a critical basis. Still other portions of the data may describe normal conditions in which no care is necessary at all. However, with the abundance of information being reported through sensor devices in the network, critical data may often become masked by other less critical data.

In one example, sensing the blood glucose of a diabetic patient may produce a large number of blood glucose readings per day. When multiple diabetic patients are each producing a similar number of readings per day and the system presents all of this data to a healthcare provider or monitoring facility, there is a substantial risk that a manual review of data might result in missing an abnormal reading embedded among the numerous readings within normal range. This problem is compounded when numerous readings of different parameters for different conditions among multiple patients are all received via a healthcare sensor network.

Therefore, there is a need to collect data via a sensor network in an efficient manner in which critical data may be effectively identified. There is also a need to identify and prioritize data such that data of higher importance may be identified and acted upon in an expeditious manner while data of lower importance may also be acted upon in a manner consistent with its level of importance.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one example, a method is provided for managing medical data from a sensor network. For example, the medical data may be received from a sensor in the network and a priority value may be generated for the medical data. The medical data may be transported to a healthcare provider based on the priority value.

In another example, the priority value may be based on the type of medical data and/or the value of the medical data. For example, the value of the medical data may be within expected normal limits or may be outside of the expected normal limits. If the value of the medical data is outside of the expected normal limits, the priority value may be further based on the amount of deviation between the value of the medical data and an expected normal value.

In another example, data may be outside of normal values, but a model of the errors in the sensor are used to appropriately interpret anomalous or out-of-bound measures, so as to appropriately interpret the data. Besides pointwise measurements, evidence about the patterns of values emitted by sensors over time may provide evidence that the sensor is failing in different ways, allowing the interpretation of the data to be continually re-adjusted to account for potential failures.

In another example, the medical data may be sorted prior to transporting to the healthcare provider. The medical data having one priority value may be transported at the top of a list of medical data and medical data having a lower priority value may be transported lower on the list of medical data.

In another example, medical data may be batched or may be filtered based on the priority value.

In yet another example, a system is provided for managing collecting medical data and transporting the medical data to a healthcare provider based on an assigned priority value.

Also, trends in changes in medical data may be identified and priority values may be assigned to medical data based on the identified trends.

In another example, received medical data may be identified as private or non-private and may be summarized or otherwise filtered. The summarized or filtered data may be transported to a healthcare provider.

In another example, reliability of sensor devices in a healthcare network may be determined and indicated with the corresponding medical data.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

A method and system for collecting, prioritizing, and/or uploading data is described. In one example, medical or health data pertaining to an individual is collected and transported based on a priority of the data. Medical data may include any type of data related to a medical condition of an individual. Also, medical data may include data pertaining to a biological condition or function of an individual. Such a biological function of an individual may be performed autonomically or voluntarily by the individual. A non-limiting list of examples of medical data includes complete blood count (e.g., hemoglobin, white blood cell count, etc.), electrolyte levels (e.g., sodium, potassium, bicarbonate, blood urea nitrogen, creatinine, etc), blood chemistries (e.g., glucose, cholesterol, triglycerides, liver enzymes, nitric oxide, etc.), blood flow parameters, cardiac rhythms/arrhythmias (e.g., electrocardiogram (EKG), rhythm strip, holter monitor, etc.), cardiac function (e.g., echocardiogram, stress test, etc.), vital signs (e.g., heart rate/pulse, blood pressure, respiration rate, etc.), body temperature, or arterial blood gas (e.g., blood pH, oxygen saturation, etc.), to name a few. In addition, medical data may include data corresponding to a condition or function of a biological specimen such as an organ or other body tissue. For example, medical data may include chemicals, gases, or other compounds or compositions produced from body tissue or organs (e.g., carbon dioxide, oxygen, methane, etc.).

Figure 1:
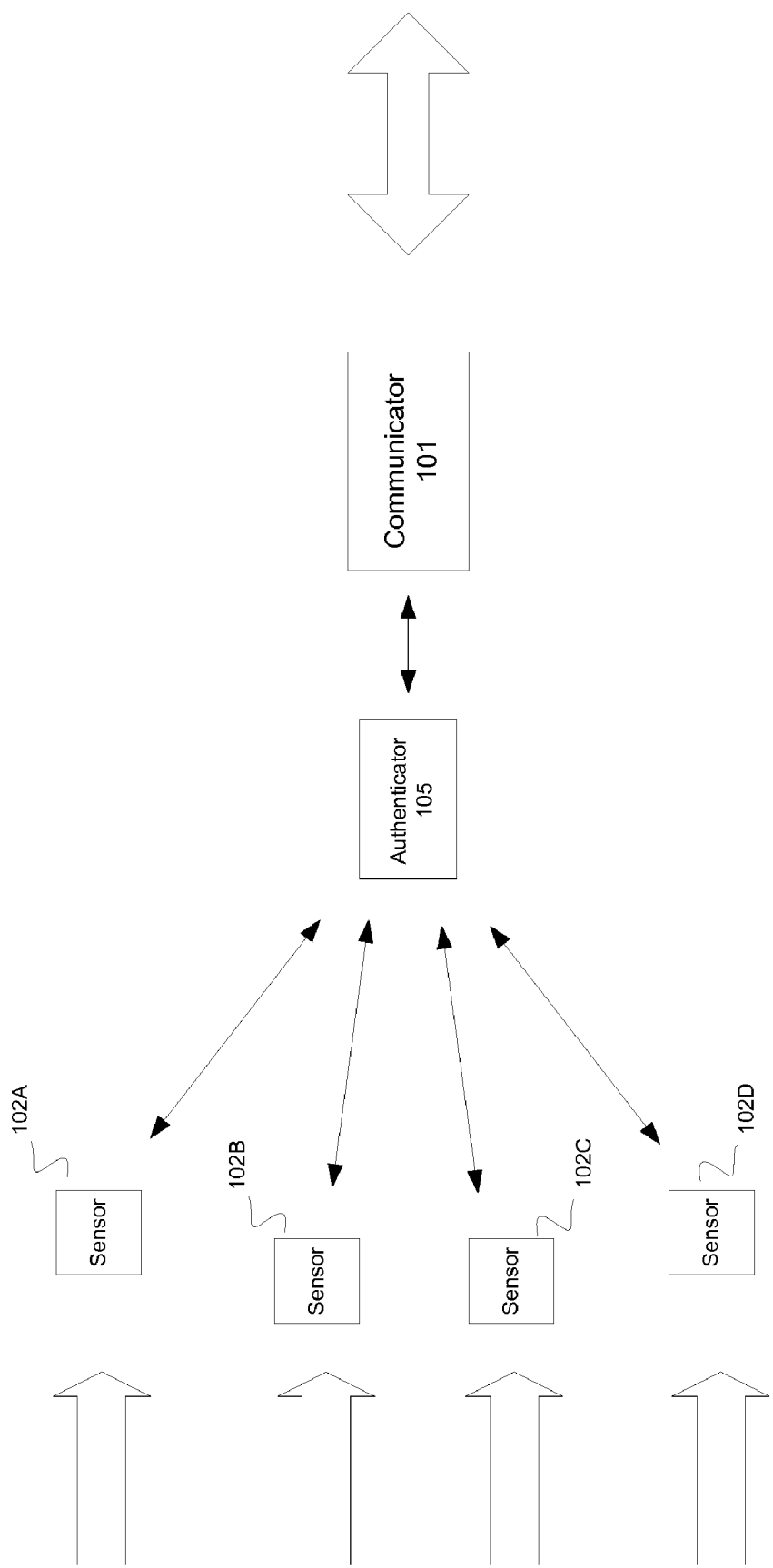
FIG. 1 is a partial block diagram illustrating a network of federated devices.

FIG. 1 is a partial block diagram illustrating an example of a network of federated sensor devices. The federated sensor devices form a sensor network in which data may be collected from the federated sensor devices and processed either in each of the federated sensor devices or in a centralized, remote location such as a communicator 101 as illustrated. The communicator 101 may further be a federated sensor device within the network that may collect data from other sensor devices and determine transport of the data received from the other sensor devices as well as data generated and/or received within the sensor devices acting as the communicator 101. Optionally, the system may include an authenticator 105 for authenticating the data, devices or entity corresponding to the data. For example, medical data may be received from sensor devices where each of the sensor devices has an associated device identifier. The authenticator 105 receives the data with the corresponding device identifier and determines access privileges of the device based on the device identifier. The authenticator 105 may contain a database, for example, storing device identifiers corresponding to trusted devices. When data and corresponding device identifiers are received at the authenticator 105, the authenticator compares the received device identifier with stored device identifiers of trusted devices. For matching device identifiers, the data corresponding to the devices with matching device identifiers is further processed. The authenticator 105 may further return a message to devices with non-matching device identifiers indicating that access is denied.

In another example, the devices sense data from an individual such as a patient and the patient may enter a password or other security input for gaining access to the system and/or entering sensed data (e.g., medical data). For example, the patient may enter a password when the sensed data is sent to the authenticator 105. The authenticator 105 determines the identity and level of access of the patient based on the password (or other security input) and permits further processing and transmission of the data based on the determination. Also, when data is prioritized and processed as described herein, the system may process a result, diagnosis or interpretation of the data. This response may be generated by a healthcare provider as described herein. To access the response, the patient may enter a password or other security input which may be received by the authenticator 105. Based on the input, the authenticator 105 may permit access to the response from the healthcare provider (or any other pertinent information) by the patient. Thus, the system may provide for access to information by authorized or authenticated entities/individuals.

Beyond authenticating potential people or destinations for analyzing raw data, and making decisions about different kinds of data streams to be shared, a patient may be comfortable only with sharing particular statistics, summaries, or abstractions of the data collected over time and/or over multiple sensors. For example, a patient may be uncomfortable sharing her ECG, but would not mind sharing data that indicated some form of dangerous QRS complex was sensed. A patient may feel uncomfortable with live feeds of glucose levels being monitored but may be comfortable with daily averages being shared. Multiple sensor-data summary, compositing, and abstraction options might be available to patients or well people that allow for the control of sharing, based on preferences and comfort about the kinds of statistics that are being shared.

One or more components that provides such conversion of sensed data or demographic data into forms that different people are comfortable with sharing with different personnel and endpoints can provide the patient with a means of being monitored for critical problems while being comfortable with sharing data. Such abstraction and creation of a composite or summary can also allow data to be shared with comfort for research purposes, thus supporting long-term longitudinal studies.

As FIG. 1 illustrates, each sensor (102A, 102B, 102C, and 102D) in the network detects a condition and receives corresponding data pertaining to the condition. Although FIG. 1 illustrates four sensor devices, any number of devices may be used. Also, any type of device may be used for collecting desired data.

Each of the sensors in this example (102A, 102B, 102C, and 102D) collects data and forwards the data to a communicator 101. The communicator 101 may further process the data received from the sensors and may send the processed data to another device, network, a hub, etc. The communicator 101 may also send the processed data to a remote server which may receive the data, back up the data, further analyze the data, aggregate the data, etc. The communicator 101 may further assign a priority to each received data and may transport the data to a remote location based on the assigned priority.

Priority may be assigned in many ways. For example, the priority may be assigned to the data based on the data itself in which a certain type of data or data reflecting certain values or other characteristics may be assigned a priority value accordingly. Priority may also be assigned dynamically to the data received from sensors or devices in the network. As one example, updated data may be received from sensors for a parameter describing a medical or health condition. The system may dynamically update the data and corresponding priority value based on the modified values received. If, for example, a blood glucose level of 90 mg/dl is initially received from a glucose monitor, a corresponding priority value may be assigned. As the value is within normal limits, the system initially assigns a low priority value to the data. If a subsequent blood glucose level of 500 mg/dl is received (not within normal limits), the system updates the corresponding priority value to indicate the critical nature of the data. Hence, a higher priority is dynamically assigned to the data based on the update. Transport of the data to the remote site (e.g., a server, hub, etc.) may be performed in accordance with the priority value. For example, data with a high priority may be transported prior to data with a lower priority. Data with very high priority may also be transported directed to a designated destination (e.g., bypass the communicator 101), if desired.

Also, the communicator 101 may sort the received data based on the priority value of each corresponding data. Thus, data may be presented at the remote site based on the priority value assigned to the corresponding data. In this case, data with higher priority value may be presented at the remote site prior to data with a lower priority value.

Figure 2:
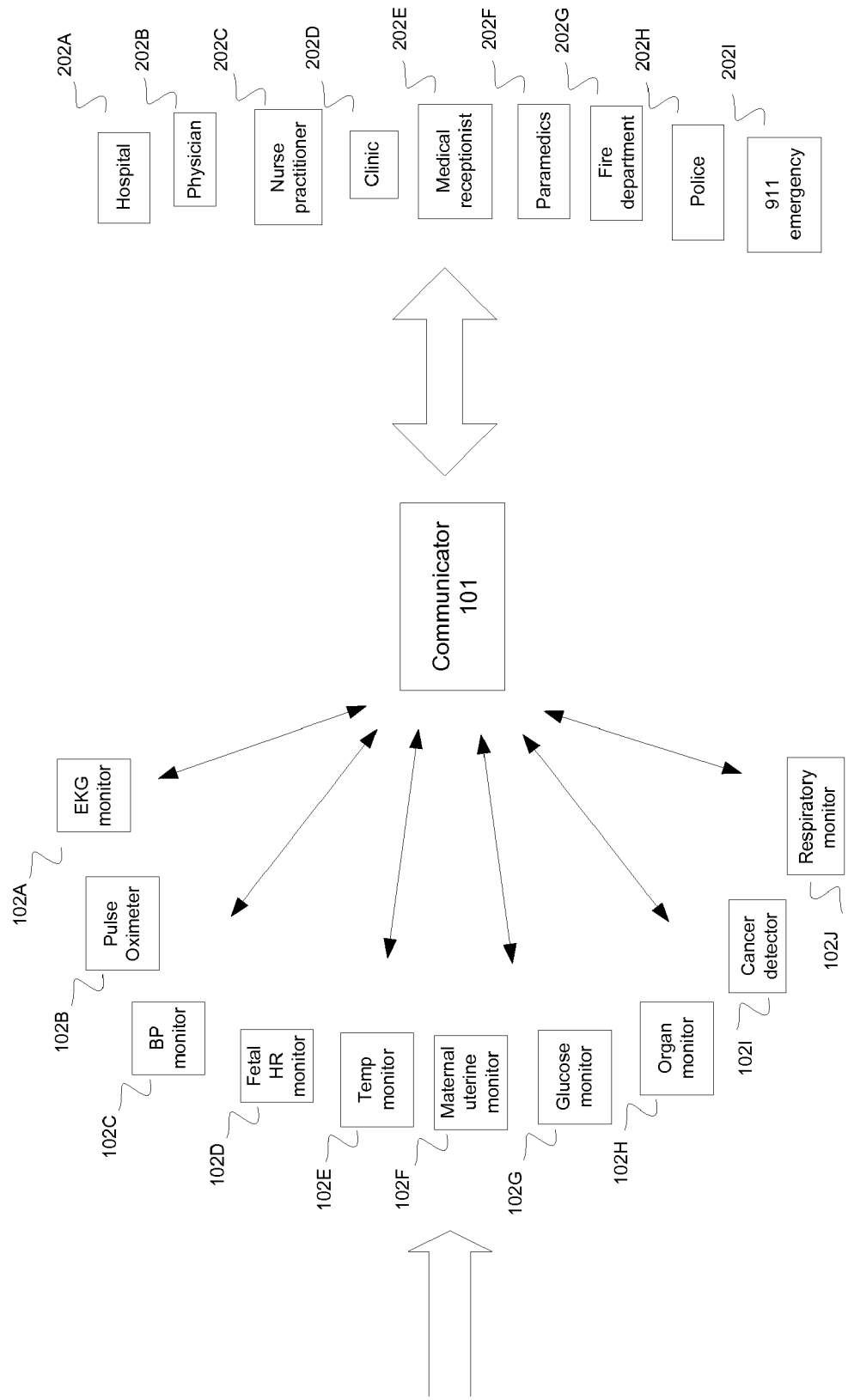
FIG. 2 illustrates a partial block diagram illustrating an example of a sensor network.

FIG. 2 illustrates a partial block diagram illustrating an example of a sensor network in which data collected pertains to healthcare of an individual. In this example, the sensor devices include an EKG monitor 102A, a pulse oximeter 102B, a blood pressure monitor 102C, a fetal heart rate monitor 102D, a temperature monitor (e.g., thermometer) 102E, a maternal uterine monitor 102F, a glucose monitor 102G, an organ monitor 102H, a cancer detector 102I and a respiratory monitor 102J. These are merely examples of medical sensor devices that may be used.

Any of these sensor devices may communicate with a communicator 101 which may further process and/or sort the data from the sensor devices. In another example, each of the sensor devices may contain a processor for processing the data such that the data may be sent directly from a sensor device in the network to a destination device. In another example, the communicator 101 may be another sensor device in the network that may further coordinate the data generated by the sensor devices in the network and may determine the method or the order in which the data is transmitted to the destination device.

Also illustrated in the example of FIG. 2 are the destination devices and entities for receiving the data generated by the sensor devices (102A-J). In this example, the sensor devices provide healthcare related information to healthcare providers or other relevant entities. The healthcare providers in this example include a hospital 202A, a physician 202B, a nurse practitioner 202C, a clinic 202D, a medical receptionist 202E, a paramedic 202F, fire department 202G, police 202H, and 911 emergency services 202I. The recipients listed here are merely examples as healthcare providers may include any relevant entity that may receive or process medical or healthcare data. For example, healthcare providers may also include a registered nurse, emergency medical technician, lab technician (e.g., clinical lab technician, radiology technician, etc.), dentist, pathologist, or physician assistant, to name a few.

The network of FIG. 2 may be used for healthcare or symptom management of patients. Parameters, observations, and other pertinent health information of a person may be collected via sensor devices in the network and returned to healthcare providers via a communicator 101. In many cases, the amount of information may become very high as more and more information is collected regarding a patient. For example, a diabetic patient may have a very high number of blood glucose values reported throughout a day (up to 1200 by some reports). In addition, other information may be received pertaining to the patient such as data relevant to other medical conditions, vital sign monitoring or the like.

As the amount of data received continues to increase, the healthcare providers receiving the information may become saturated with data. Thus, in this example, the communicator 101 may further process the data prior to transmitting the data to the healthcare providers. In one example, the communicator 101 may assign a priority value to each of the data received from the sensor devices. Based on the assigned priority values, the corresponding data may be transported to the remote devices. The priority values assigned to the entities may be determined based on the kind of data and values of the data. For example, if an EKG monitor senses dangerous changes in the EKG of a patient, the communicator 101 may assign a high priority value to the data and may transport this (critical) data prior to transmitting data of lesser importance (and with a lower priority value). Likewise, if other readings are detected that are out of range of normal limits, this information may be assigned a higher priority value depending on which parameters are outside of normal limits and how far out of the normal limits the parameters are. If the values are borderline, then the data may be assigned an intermediate value for a priority. If the values are grossly out of range, a higher priority value may be assigned. If the values are within normal limits, then a very low priority value may be associated with the data. Alternatively, data with very low priority values may be filtered.

In another example, the priority of data from one sensor may affect the priority of data from another sensor. The data collected and provided from a first sensor may be related to data collected and provided from a second sensor. If it is determined that the data from the first sensor has high priority, then the data from the second sensor that is related to the data from the first sensor may be assigned a high priority also. In this way, related data may be assigned high priority if any portion of the data has high priority. Hence, the healthcare provider is less likely to miss an important finding. As an example, a first sensor may provide serum glutamate pyruvate transaminase (SGPT) of a patient, a second sensor may provide serum glutamic oxaloacetic transaminase (SGOT) of the patient, and a third sensor may provide an alkaline phosphatase of the patient. The three parameters from the first, second and third sensors are liver enzymes that may be elevated in various liver conditions.

The system receives each of the SGPT, SGOT, and alkaline phosphatase data for the patient, of which the SGPT may be elevated in the patient. Based on the elevated SGPT, the system assigns a high priority to the SGPT data and also determines that SGPT from the first sensor is related to the SGOT from the second sensor and the alkaline phosphatase from the third sensor. In this example, the system assigns a high priority to the SGOT and alkaline phosphatase data corresponding to the SGPT data. Thus, in this example, even if the data from the second and third sensors indicate that the SGOT and the alkaline phosphatase are within normal limits, the priority for each of the SGOT and the alkaline phosphatase values corresponds to the priority assigned to the elevated SGPT data because of the determined relationship between the data. In this way, related data may be assigned corresponding priority values based on the state of any one of the data in the group of data.

In another example to illustrate, increasingly critical information may be transmitted with high priority with related data. For example, an abnormality detected in a rhythm strip or ECG may indicate a possibility of a myocardial infarction in progress (e.g., the appearance of Q waves). Being a critical parameter in this example, the rhythm strip or ECG data may be assigned a high priority for transmission to a health care provider. In one example, CPK-MB values for the patient may be within normal limits even though a rhythm strip or EKG tracing may indicate the presence of a myocardial infarction. However, the CPK-MB value, also being related to cardiac function, may also be assigned a high priority and transmitted to the health care provider. Thus, the priority status of one parameter in a group of related parameters may affect the priority status of other parameters in the group, In addition, the system may determine relationships between the received data from the different devices or sensors and process the data and assign priorities to the data based on the determined relationships. For example, a blood pressure monitor may return a blood pressure reading and a heart rate/pulse monitor may provide data pertaining to the heart rate of a patient. The system may determine that a relationship exists between the blood pressure and heart rate of a patient. For example, when the blood pressure decreases, the heart rate may increase proportionately. Hence, the system may determine that the blood pressure and heart rate parameters have a relationship and may store the relationship such that priority values may be assigned to each of the related parameters accordingly.

The system may further be capable of determining the relationships of parameters based on the values of the parameters received. For example, the system may receive a blood pressure reading from a patient that is lower than normal. Also, the system may receive a heart rate reading that is higher than normal for the patient. The relationship between the blood pressure and the heart rate may be stored on different readings of the parameters and a relationship may be determined. In this case, an inverse relationship may be determined by the system between blood pressure and heart rate. The system may automatically assign a relationship between the parameters such that similar priority values may be assigned to each of the related parameters by the system, with the relationship being determined by the system. Hence, the healthcare provider would be better equipped to manage, diagnose, or treat the patient having received both related parameters with similar priority values.

Hence, the recipient of the data (e.g., hospital 202A, physician 202B, Nurse practitioner 202C, clinic (202D), medical receptionist (202E), paramedic (202F), fire department (202G), police (202H) and/or 911 emergency services (202I)) may receive prioritized data from the communicator 101 (or from any of the devices in the network). For example, high priority data may be transmitted from the communicator 101 prior to lower priority data. In another example, low priority data may even be filtered at the communicator 101 and may be stored at the communicator 101 or at a remote storage site. Hence, the healthcare provider may receive only high priority information without being distracted by low priority data.

In yet another example, the data may be sorted in the communicator 101 based on the assigned priority values for the data. Hence, the communicator 101 may assign a priority value to each of the received data from the sensor devices in the network and may place the high priority information near the top of the list of information. In this case, the healthcare professional may receive the data in order of importance.

Figure 3:
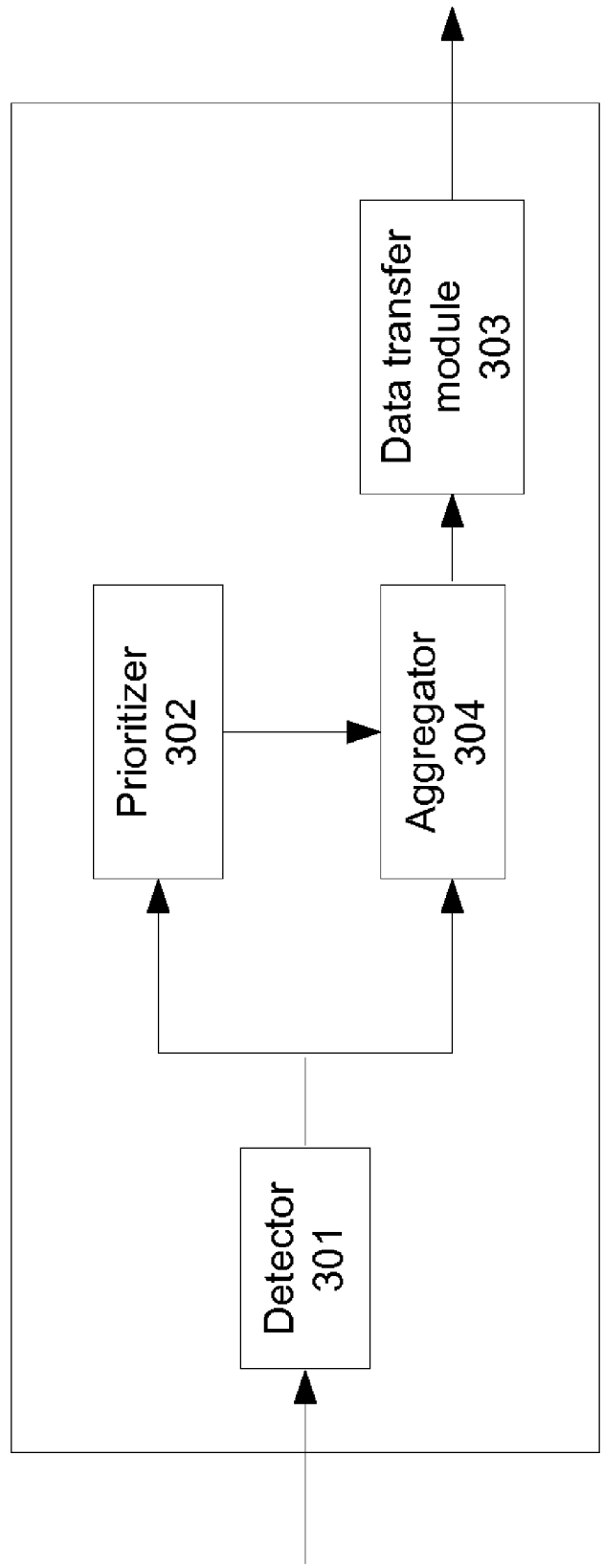
FIG. 3 is a partial block diagram illustrating one example of a communicator.

FIG. 3 is a partial block diagram illustrating one example of a communicator 101. In this example, the communicator 101 contains a detector 301 for detecting information received from network devices. The information may further be sent to a prioritizer 302 for assigning a priority to the information. In the prioritizer 302, a priority value may be assigned to the information based on the nature of the information. For example, if healthcare information is received for a patient, the type of healthcare information and the values corresponding to the information may be used to determine the priority of the information. In one example, the healthcare information includes electrocardiogram tracings (EKG). If no abnormalities are detected in the EKG by the detector 301, then a lower priority value may be assigned to the data. If, however, abnormalities are detected in the detector 301 such as elevated or depressed S-T segments, inverted T waves, prolonged P-R intervals or Q-waves indicating the possibility of a myocardial infarct, then a higher priority value may be assigned to the data. Likewise, if one of the sensors in the sensor network is a pulse oximeter, the detector 301 may receive a reading from the pulse oximeter indicating that the oxygen saturation of the patient is less than 70%. In this case, the value is grossly below normal such that the prioritizer 302 may assign a high priority value to the data.

The communicator 101 may further include an aggregator 304 for aggregating the data received from the network devices. The data may be aggregated according to the assigned priority values for each of the corresponding data. The aggregator 304 receives the data from the detector 301 and may further receive a corresponding priority value from the prioritizer 302. The aggregator 304 further processes and organizes the data received from the sensor devices according to corresponding priority values received from the prioritizer 302. For example, data may be received from a glucose monitor in a diabetic patient. The glucose reading may be greater than 500 mg/dl. The data may be detected by detector 301 and may be assigned a corresponding priority value in the prioritizer 302. In this case, the prioritizer 302 may determine that the glucose level in the patient is high. For example, the prioritizer 302 may access a database of ranges of glucose values including normal ranges and abnormal ranges. Based on the data obtained, the prioritizer 302 may determine that the data is out of the normal range and may consequently assign a high priority value to the data.

Also, the data may be received at the aggregator 302 with a corresponding priority value determined in the prioritizer 302. The aggregator may further process or organize the data based on the priority value. For example, the aggregator 304 may receive the high priority value from the prioritizer 302 and in response to the high priority value, may contact emergency services directly. In this case, the glucose value of the patient may be considered very high as to be life-threatening such that the priority value assigned by the prioritizer 302 may be set such that the aggregator 304 is informed as to the critical nature of the data. Hence, the aggregator 304 contacts emergency services and initiates emergency procedures for the patient. Alternatively, the aggregator 302 may send the data to a data transfer module 303 for transmitting the data to a healthcare professional. It is noted that any subunit of the communicator 101 as illustrated in FIG. 3 may be incorporated into any other subunit of the communicator 101. For example, the aggregator 302 may be incorporated in the data transfer module 303 as a single unit. Also, the prioritizer 302, aggregator 302, and data transfer module 303 may be merged into a unit.

The healthcare provider may further be selected based on the priority value assigned by the prioritizer 302. For example, the glucose data received and detected by the detector 301 and assigned a priority value by the prioritizer 302 may be associated with an endocrinologic condition. The data transfer module 303 may thus send the data to an endocrinologist. Likewise, based on the priority value, the data may be sent to any number of other healthcare professionals such as a nurse practitioner, 911 emergency services, hospital, etc.

Figure 4:
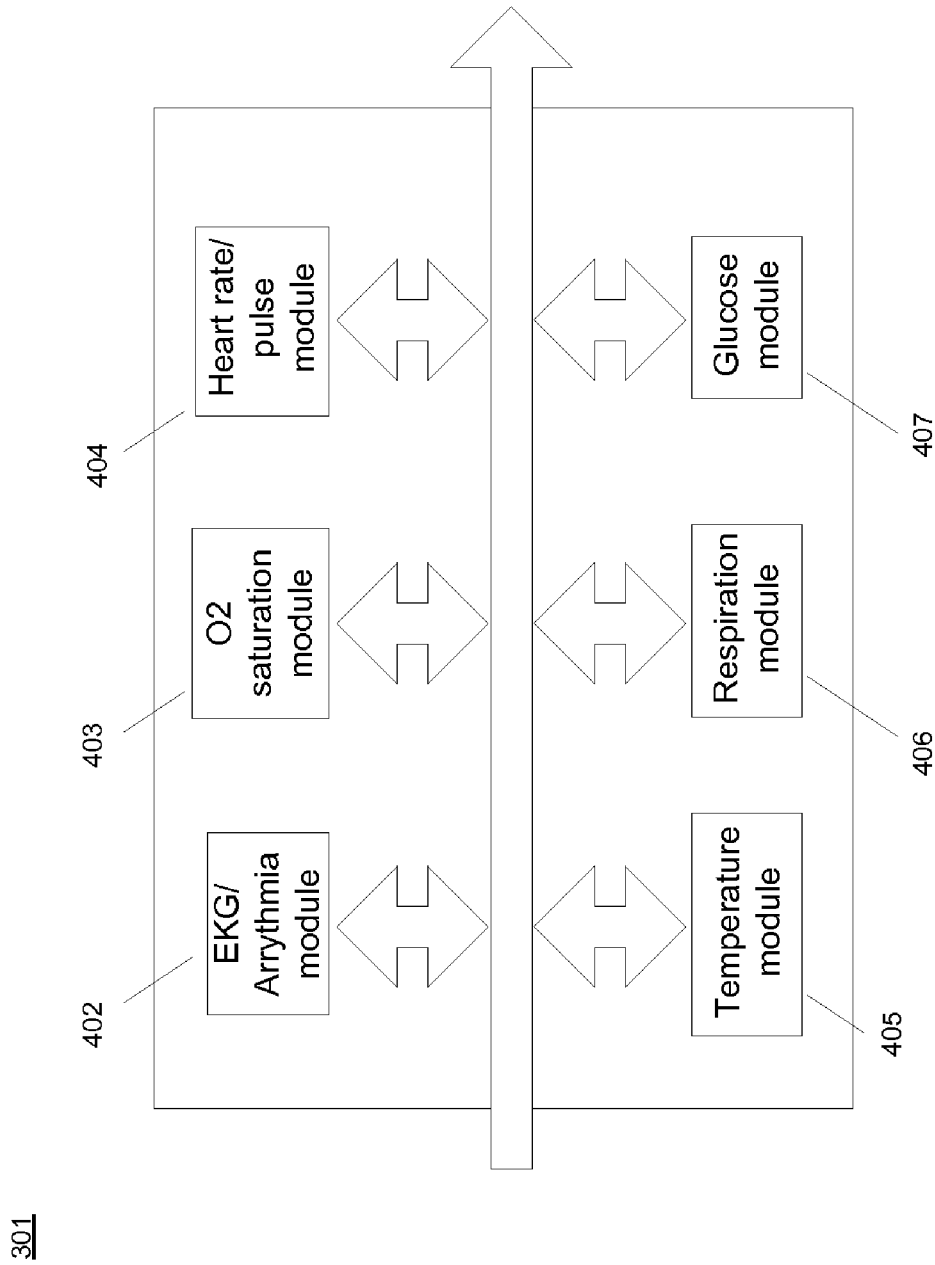
FIG. 4 illustrates one example of a detector for detecting and categorizing received information.

The detector 301 detects the data received at the communicator 101 and may further categorize the data such that a corresponding priority value may be assigned in the prioritizer 302. FIG. 4 illustrates one example of a detector 301 for detecting and categorizing received information. In this example, data is received and categorized as to type of data. For example, a rhythm strip may be received (i.e., EKG tracing) and may be identified by an EKG/arrhythmia module 402 in the detector. Oxygen saturation received from a pulse oximeter may be identified by an oxygen saturation module. Also, a heart rate/pulse module may identify pulse information. Temperature may be identified and categorized by a temperature module 405, respiration rate data may be identified by a respiration module 406 and blood glucose values may be identified by a glucose module 407. FIG. 4 is only a partial block diagram illustrating representative modules. Other modules may be present to identify any relevant data of interest.

When data is detected in the detector 301, the data may be categorized and identified as to the type of data. The data in the prioritizer 302 may include the identification as to the type of data such that the prioritizer 302 may be able to classify the data as high priority or data with lower priority. The prioritizer 302 may be set for any number of priority levels and the prioritizer 302 may set a priority value accordingly. For example, one of two levels of priority values (high and low) may be assigned to any data. In another example, one of three levels of priority values (e.g., high, medium, low) may be assigned to any data. In yet another example, one of four levels of priority values (e.g., critical, important, average, low) may be assigned to any data. Also, five levels of priority values (e.g., extra critical, critical, high average, low average, low importance) may be assigned to any data. The foregoing are merely examples as any number of levels of priority may be assigned to the data.

Based on the categorization of data in the detector 301, the prioritizer may identify normal ranges of values for the type of data received. The prioritizer 302 may further retrieve normal ranges of values for the corresponding type of data from a database and may thus identify values of received data that are out of the normal range. Also, after comparing the received data with values retrieved from the database, the prioritizer may determine the degree of abnormality of received values. Based on the degree of abnormality of the received data, the prioritizer 302 may assign a corresponding priority value.

Figure 5:
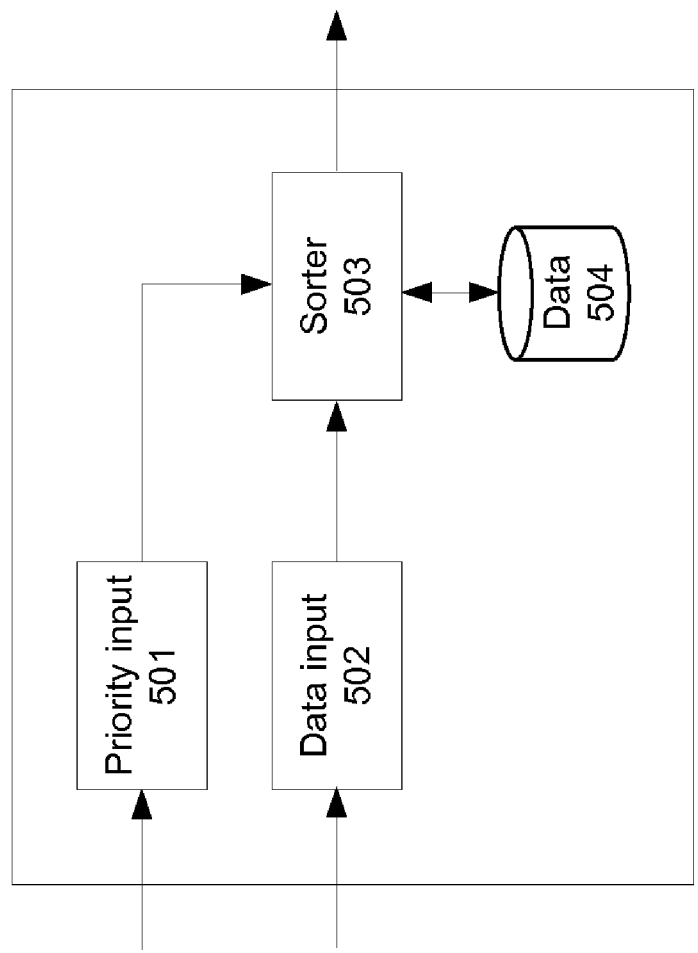
FIG. 5 illustrates a partial block diagram of an aggregator for sorting data based on a corresponding priority value.

The aggregator 304 receives the data and the corresponding priority value from the prioritizer 302 and may further process the data based on the corresponding priority value. For example, the aggregator 304 may sort the data based on the priority values and may present the data such that high priority data is reported at the top of the list. FIG. 5 illustrates a partial block diagram of an aggregator 304 for sorting data based on a corresponding priority value. In this example, the aggregator 304 contains a data input 502 for receiving data. The data received at the data input 502 contains information received from sensor devices in the network. The information may include patient healthcare data such as blood glucose levels, EKG readings, oxygen saturation, etc. Also, the aggregator 304 may receive priority values corresponding to the data received. The priority values may be assigned in a prioritizer 302 based on a type and value of the data received. The assigning of a priority value may also include comparing the value of the received data with data stored in a database to determine if the received data falls within a normal range of values and if not, the degree to which the value falls outside of normal limits.

The aggregator 304 receives the data (e.g., via the data input 502) and the corresponding priority value (e.g., via the priority input 501) and may sort the data received in a sorter 503. For example, the sorter 503 may sort data received based on the priority values of each of the corresponding data. Data may be further stored in a database 504 for later sorting with other received data. For example, if a first data is assigned a low priority value, the sorter may store the data in the database 504 for later transmission. If a second data is received that is assigned a high priority value, the sorter may place the second data above the first data in priority and may transmit the first and second data with an indication that the second data has higher priority. For example, the first and second data may be transmitted on a list with the second data being higher on the list than the first data. Alternatively, the second data may be marked such that the transmitted data contains an indication that the second data has high priority. Thus, the healthcare provider or facility may respond to the data accordingly.

Figure 6:
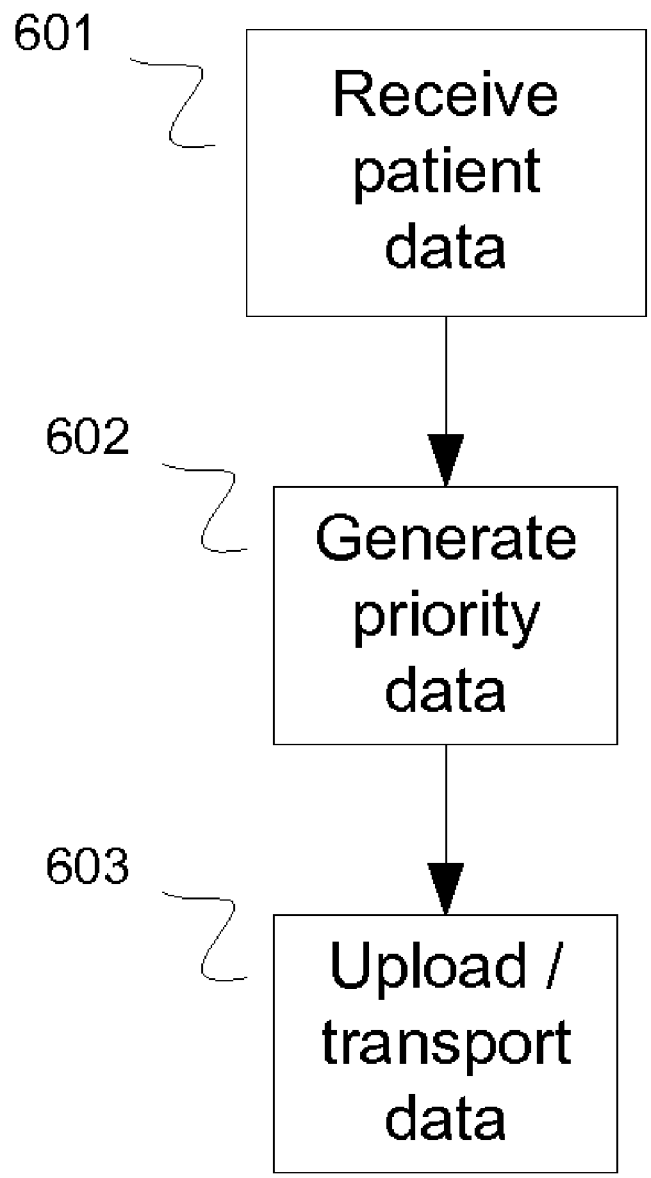
FIG. 6 is a flowchart illustrating an example of a method for obtaining and transporting healthcare data from a subject.

FIG. 6 is a flowchart illustrating an example of a method for obtaining healthcare data from a patient and transporting the data to a designated destination. In STEP 601, patient data is received. The patient data may be collected from at least one sensor positioned on or in the vicinity of the patient. For example a pulse oximeter may be attached to a patient for providing data on the blood oxygen saturation of the patient. Also, a blood pressure monitor, electrocardiogram, or glucose monitor may be connected to provide corresponding readings for the patient. The readings from each of the devices may be obtained periodically or continuously and may be returned to a central device for further processing such as assigning a priority value (STEP 602). Alternatively, each of the devices may include a component for determining a priority value associated with the corresponding data. In one example, data may be given a high priority based on whether the data is within normal limits. If the value of a reading is out of normal limits, the data may be assigned a high priority and may be assigned a lower priority if within normal limits. Also, the priority value may be higher or lower depending on the degree to which the value is out of normal limits. For example, if the value is greater than 10% out of normal limits, a first priority value may be assigned and if the value is greater than 50% out of normal limits, a second priority value may be assigned, which is greater than the first priority value.

Based on the priority value, the corresponding data may be transported or uploaded to a destination (STEP 603). Also, a method of transporting the data may be determined based on the priority value. For example, data with a low priority value (e.g., data within normal limits) may be stored and batched for subsequent uploading to the destination (e.g., hospital, physician's office, etc.). Data with high priority may be uploaded or transported to the destination immediately. Also, in a case where the data has a priority value indicating very high priority, the corresponding data may trigger an immediate connection with emergency services. As one example, a diabetic patient may return a blood glucose reading of 1000 mg/dl which may be determined to be a life-threatening situation. In this case, emergency services may be called directly.

Figure 7:
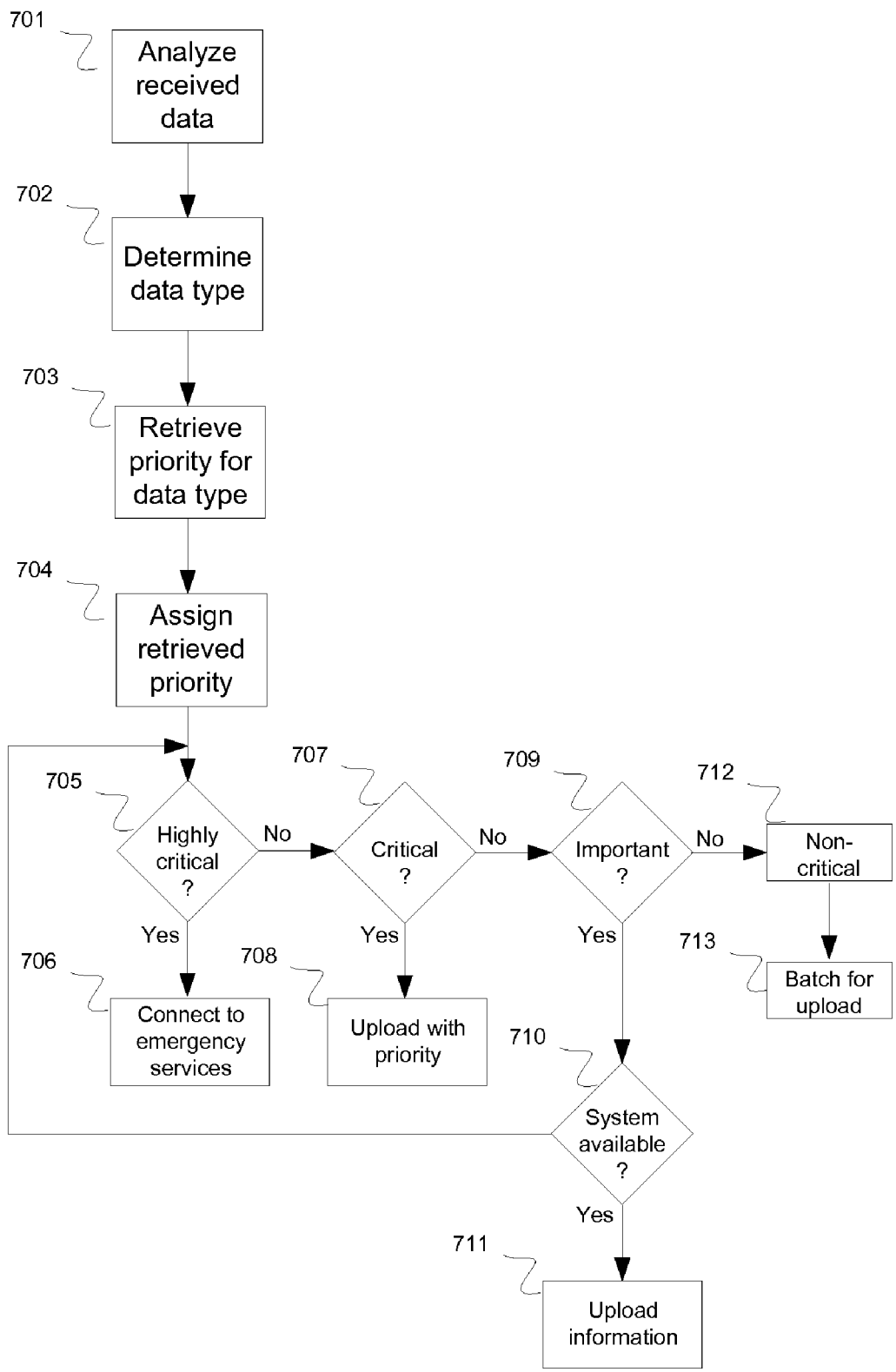
FIG. 7 is a flowchart illustrating an example of generating priority value for data.

FIG. 7 is a flowchart illustrating an example of generating priority values for data. In STEP 701, the data received is analyzed. The data received may include healthcare data for a patient and the analysis may include determination of the type of data (STEP 702). For example, the data may be determined to be EKG data of a cardiac patient. Additionally, the data may be analyzed to determine if an abnormality exists in the data. For example, if the data received is EKG data, then the EKG data may be analyzed to determine if an arrhythmia exists or other indication of pathology. As one example, the EKG may indicate that a myocardial infarction may be occurring or has occurred. In this case, corresponding abnormalities in the EKG (e.g., inverted T waves, elevated or depressed S-T segments, Q-waves, etc.) may be detected. Based on the analysis of the data, a priority may be determined for the data (STEP 703).

In STEP 703, a priority value is retrieved for the data based on the type of data. Also, the priority value may be based on the value or state of the data. Based on the type of data, a database may be accessed to determine a range of normal values for the type of data. As one example, if the type of data is determined to be blood glucose readings from a patient, a database may be accessed to determine a normal range of blood glucose values. Also, the database may include any number of ranges out of the normal range and may correlate each of the ranges with a corresponding priority value. For example, values within normal limits may have a corresponding low priority, values outside of the normal range but within 10% of normal may be assigned a higher priority, whereas values outside of 10% of normal but within 30% of normal may be assigned an even higher priority. Values that are out of the normal range by 30% or greater may be assigned a highest priority. Hence, a range of priority values may be available for assigning to a given received value of a particular type based on the type and based on the value of the data and the relationship between the value of the data and the expected normal range of values.

In STEP 704, a corresponding priority value is assigned to the data as described. Based on the priority value, the data may be processed accordingly. Any number of priority levels may be used. In the example illustrated in FIG. 7, 4 levels of priority are illustrated, however, any number of priority levels may be used in practice. In the example of FIG. 7, four levels of priority are used—highly critical, critical, important and non-critical (in order of descending importance). If the priority value is of the highest priority (e.g., "highly critical" in this example) ("YES" branch of STEP 705), then the patient may be connected directly to emergency services (STEP 706). One example is if the data received indicates a life-threatening situation in which immediate medical attention is desired (e.g., ongoing myocardial infarction, diabetic ketoacidosis, etc).

If the priority value is high but not as critical ("YES" branch of STEP 707), then the data may be uploaded or transported with the priority value (STEP 708). Thus, a recipient of the data, such as a healthcare provider, may act on the data accordingly with high priority. One example may be if the data received indicates an important situation that may not be immediately life-threatening but may still require medical attention. For example, the data received may be a blood glucose of 180 mg/dl which is out of the normal range and needs medical attention but is not likely to be immediately life threatening.

If the priority value is high but not critical and does not need immediate medical attention ("YES" branch of STEP 709), then if the system is available ("YES" branch of STEP 710) the system may upload or transport the data to the recipient. However, if the system is busy ("NO" branch of STEP 710), then the system may wait until the system is not busy before sending the data. For example, if more critical data needs to be managed first, then the system may process the other data of higher priority first before processing (uploading or transporting) the lower priority data. One example may be if the data received is within normal limits but is borderline. For example, the data received may be an oxygen saturation reading from a pulse oximeter of 90%. In this case, the value is within normal limits but is borderline low. Thus, the system may wait for an opportunity to upload or transport the information as soon as possible but may give priority to data determined to be of higher priority.

If the priority value is low indicating that the data is non-critical (STEP 712 and "NO" branch of STEP 709), then the data may be batched for later uploading. For example, the data may indicate a normal reading of a parameter of a patient such that it would be unlikely that a physician would take immediate action based on the data. In this case, the data may be either transmitted when an opportunity exists or may be batched such that all such collected data may be transmitted together at a later time. Because this information is determined to be of low importance and of low clinical value, the information need not be transported on an emergency basis and data of higher priority may take precedence over the low priority data.

Figure 8:
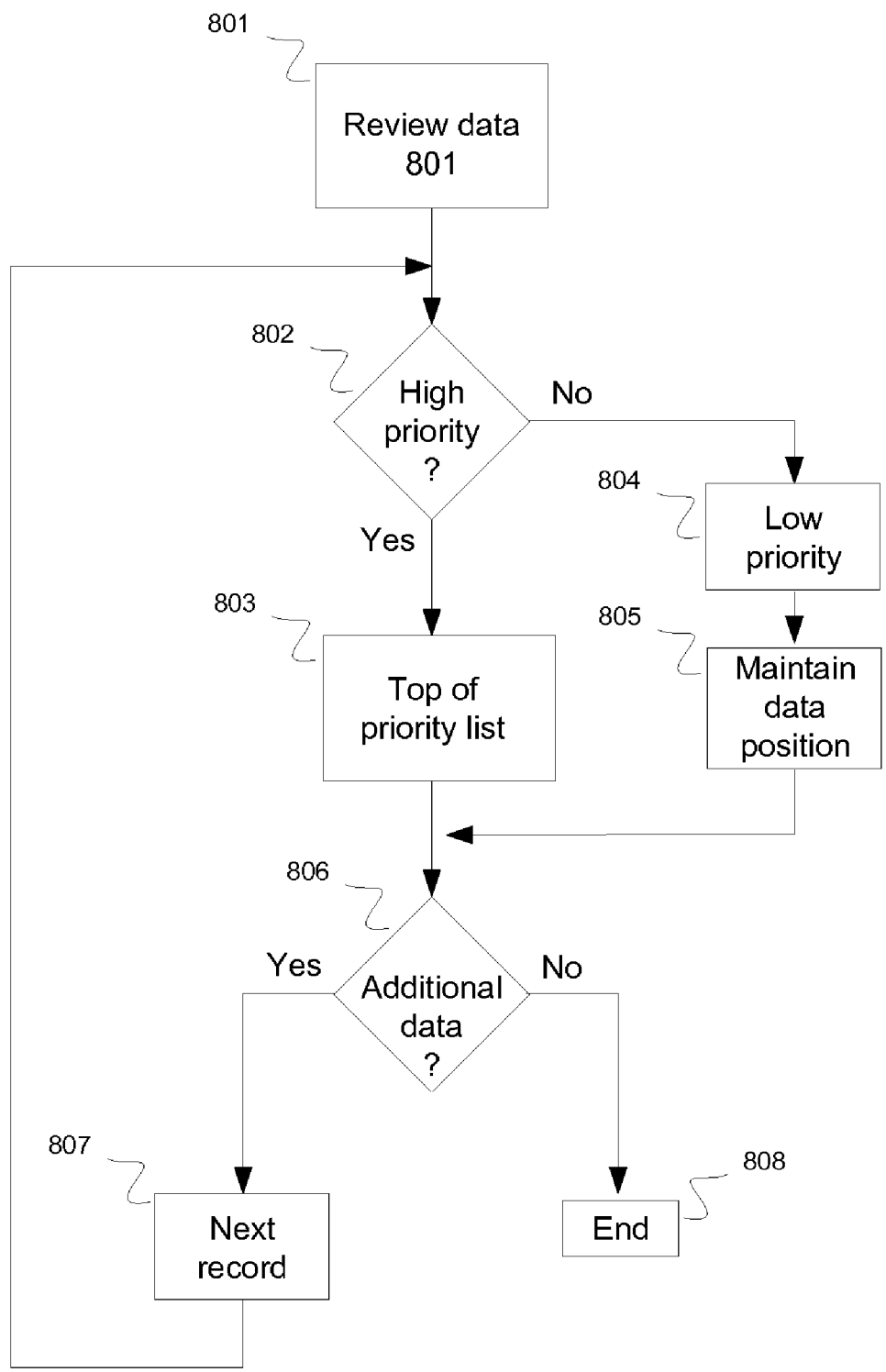
FIG. 8 is a flowchart illustrating an example of sorting prioritized data for transmitting to a recipient.

In another example, data may be assigned a corresponding priority value and may be sorted with other data prior to transmission to the destination (e.g., healthcare facility or provider). FIG. 8 is a flowchart illustrating an example of sorting prioritized data for transmitting to a recipient. In STEP 801, data is received and reviewed for data type and priority. For example, a type of data may be identified and a database may be searched for a normal range of values for the type of data as described. Based on the value of the data with respect to the type of data, a corresponding priority value may be assigned to the data. If the priority value indicates that the data has high priority ("YES" branch of STEP 802), then the data is sorted with other data as high priority. Thus, in this example, the high priority is moved to the top of the list of data (STEP 803). If additional data is present ("YES" branch of STEP 806), then the process repeats from STEP 802 in which the priority value of the next data is examined. If the priority of data is of low priority ("NO" branch of STEP 804), then the data is not moved to the top of the priority list but is maintained at a current location within the list of data (STEP 805). Alternatively, the data may be moved to a lower position on the list such as the bottom of the list. The process repeats until each set of data is examined, assigned a priority value, and sorted in the list of data ("NO" branch of STEP 806, STEP 808). Also, data of very low priority may be filtered such that the very low priority data is removed from the list and not transported to the destination at all. Rather, the data may be stored in a database either locally or remotely and may be accessed, if desired, at a later time. Alternatively, the data determined to be of very low priority may be batched together and sent to the recipient at a later time.

Hence, in this example, data of higher priority "bubbles up" to the surface of a list of data such that a recipient of the data, such as a healthcare provider receiving data from a patient, may receive data that is pertinent in a way in which the data is easily accessible. Thus, the healthcare provider may be more readily equipped to provide needed healthcare based on the data received rather than become overwhelmed by large volumes of poorly organized data.

In another example, priority may be assigned based on changes detected in patient data. In this example, medical data may be received from a subject or patient and stored. Also, the received medical data may be compared to previously stored data for the subject. For example, the medical data may be compared to previous corresponding data and changes in the data may be identified. Based on the comparison of the medical data, a relevance value or factor may be assigned to the received medical data. A priority value may be assigned to the received medical data based on the relevance value or factor.

As one example to illustrate, a blood glucose level may be received for a patient which is within normal limits. This data may be stored either locally or remotely and may be accessed at a subsequent time if desired. At a subsequent time, an updated and current blood glucose level may be received for the patient that shows an increase in the glucose level but still within normal limits. The system may further determine the extent of the change in the data which may also include a time factor. For example, the system may determine the amount of change of the data over a certain period of time and based on the determination may identify the change in data over the period of time to be predictive of potential health problems downstream. Based on this determination, the system may assign a corresponding relevance value or factor to the received medical data. For example, if it is determined that the medical data, even though within normal limits, may signal a potential health problem given the trend of the changes in the values of the data, then a high relevance factor may be assigned. Conversely, if the trend of the change of values of the data is determined to be insubstantial, for example because the change is smaller than a predetermined threshold amount and/or the change in values is smaller than a predetermined threshold amount over a predetermined period of time, then a low relevance factor may be assigned.

In this example, a priority value may be assigned to the medical data based on the relevance factor. Thus, even if received medical data is within normal limits, the priority value assigned to the medical data may still be high if changes in the values of the data is detected and the changes in the values of the medical data indicate a trend in which the likelihood of potential health problems downstream are deemed likely. In this way, the health response to patient data may be proactively enhanced.

Figure 9:
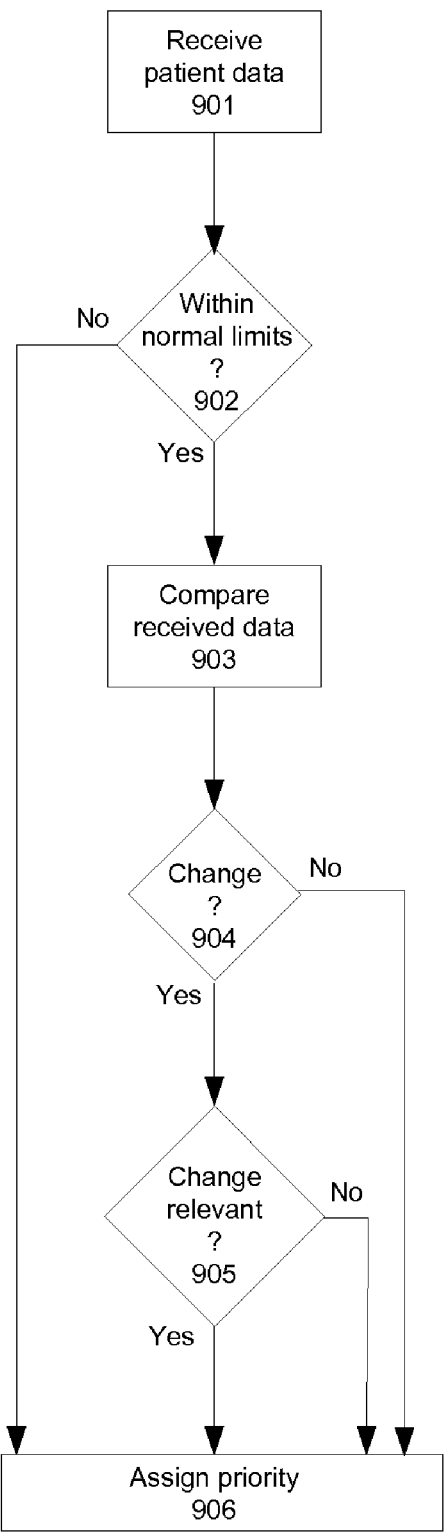
FIG. 9 is a flowchart illustrating an example of determining priority of data based on trends in changes of the data.

FIG. 9 is a flowchart illustrating an example of proactively enhancing the safety and health response to patient data. In this example, patient data is received (STEP 901) and compared to previously received or stored patient data. Also, the received patient data may be compared to normal ranges of the corresponding data (STEP 902). If the data received is determined to be out of normal range, then a corresponding priority may be assigned to the patient data. For example, if the received patient data is considered out of normal range, the patient data may be assigned a high priority value. Conversely, if the received patient data is considered to be within normal range ("Yes" branch of STEP 902), the patient data may be compared to a previously captured value corresponding to the patient (STEP 903). For example, the received data may include a patient identifier such that the system may match the received data with the corresponding values previously received for the patient. In addition, if desired, the patient data may also contain an identifier indicating the type of data received. The data may thus be matched with data of like type.

Based on matching the received data with the previously received data (i.e., stored data of the patient), the data may be assigned a corresponding level of priority or alerting. For example, comparison with previous data may indicate that a change has occurred in the patient data ("Yes" branch of STEP 904). The change may be within normal limits ("Yes" branch of STEP 902), however may indicate by the trend of the change of value of the data that potential problems may occur over time. Hence, relevance of the change in patient may be assessed by the system (STEP 905). For example, a rising blood urea nitrogen level, creatinine level, and/or potassium level in a renal patient may indicate that renal function is further compromised or that dialysis may be indicated either presently or downstream. By observing trends in changes in certain values, the system heralds problems coming downstream. In addition, the potential problems may be further categorized as to certain periods of time. Based on this information, a corresponding priority value may be assigned to the data (STEP 906).

Hence, if the change is detected in the patient data as compared to previously received data ("Yes" branch of STEP 904), the system may further characterize the relevance of the change in values (STEP 905) and a corresponding priority value may be assigned based on the trend of the change of patient data and/or relevance of the change in values (STEP 904, STEP 905, STEP 906).

In another example, data security may be enhanced via preprocessing of patient data. In one example, medical data may be received from a subject or patient including a preference from the subject. The preference may be provided in a preference profile indicating medical data to be kept private. For example, a patient may wish to keep a portion of the medical data private such that third parties do not have access to the private portion of the medical data. At the same time, there may be other portions of the medical data (i.e., non-private portions) that the patient agrees to share with others. Hence, the private portions of the medical data may be further processed to ensure data security while the non-private portions may be transmitted to the healthcare provider in substantially the same form as it is received.

Thus, in this example, medical data may be received with a preference profile indicating the level of privacy of the medical data. Alternatively, the preference profile may have been received previously and stored locally or remotely. In this example, when medical data is received, the previously stored preference profile may be accessed to determine which portions of the medical data is considered private and which portions of the medical data is considered non-private. By comparing the received medical data with indications of preferences of private data in the preference profile of the patient, the system may identify private data and may further filter the identified data. In filtering the data, the system may protect the privacy of the patient.

Filtering the data may include any number of methods for protecting the privacy of the patient. In one example, the filtered data may be summarized such that the actual data is not transported over the network but rather a summary of the data is transported. The summary may include an overview of the medical data, trends in the data, or other indication of health-related conditions of the patient without disclosing details. Alternatively or additionally, the filtered data may include a composite of data in which key portions of the information are combined to form a composite of data for transporting to the healthcare provider. As one example, abnormal values of certain parameters may be filtered while a composite list of parameters (without actual values) may be transported to the healthcare provider. Hence, medical data security of a patient or subject may be maintained.

Figure 10:
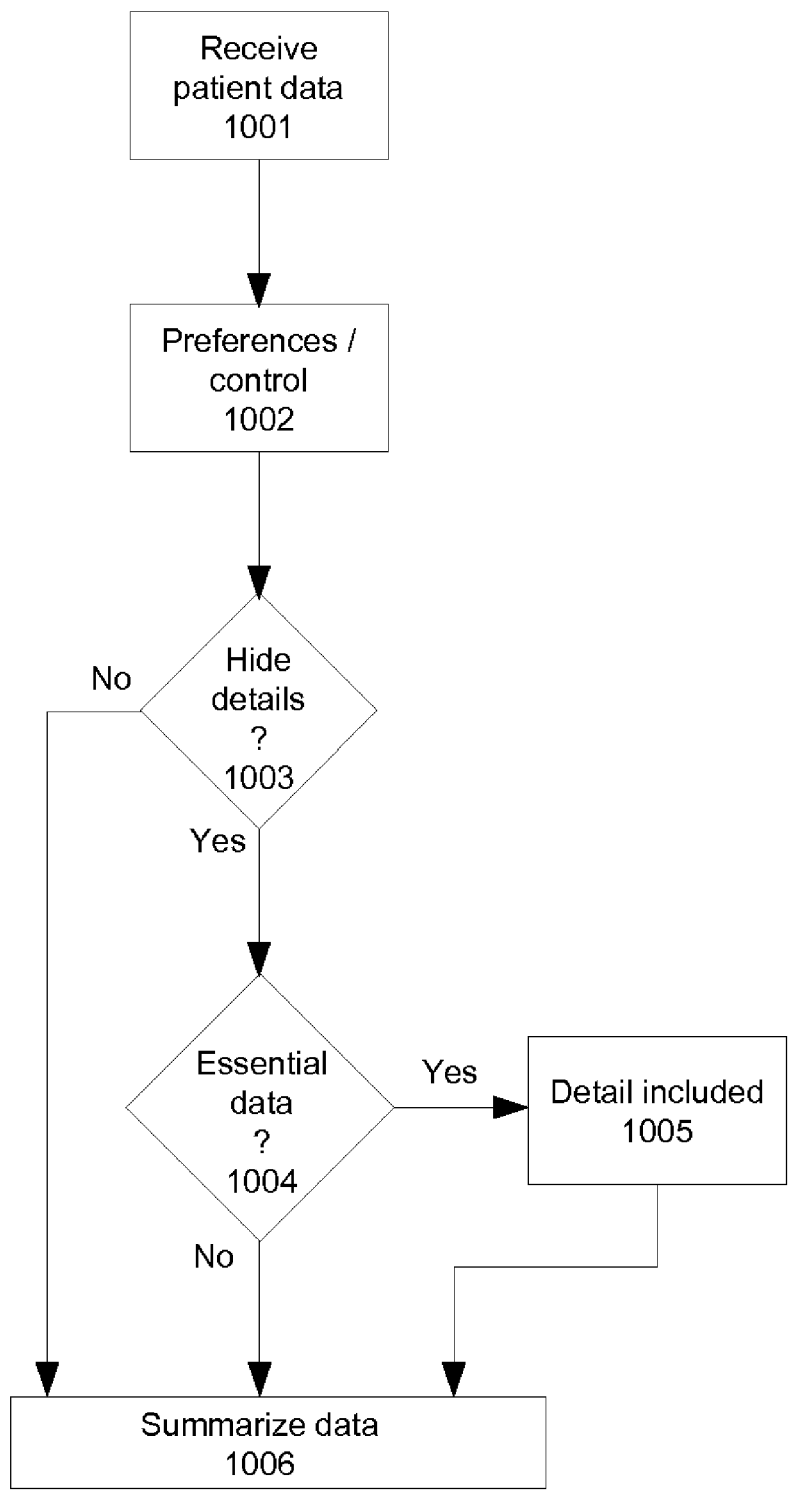
FIG. 10 is a flowchart illustrating an example of increasing data security while maintaining effective patient monitoring Like reference numerals are used to designate like parts in the accompanying drawings.

FIG. 10 is a flowchart illustrating an example of increasing data security while maintaining effective patient monitoring. In STEP 1001, patient data is received. The patient data may include any type of patient data such as non-sensitive information that a patient may not object to sharing or sensitive information that a patient may wish to keep confidential. In one example, (STEP 1002), the patient may provide preferences of information that is desired to keep confidential and/or an indication of data that the patient may determine to be non-sensitive. This information may also be received from the patient. Also, information may be stored at the system indicating default values for data confidentiality. Thus, if a patient does not provide preferences, any of the information may be characterized as sensitive or non-sensitive based on statistical averaging of random patients.

Based on the preferences or other control received from the patient or otherwise obtained at the system (STEP 1002), the system may prepare to conceal certain types of information deemed private (STEP 1003), Thus, the patient data may include sensitive data and non-sensitive information based on patient preferences or other control command or indicator received at the system. If a particular patient data is deemed non-sensitive, then the identified data may be included in a data transmission to a health care provider ("No" branch of STEP 1003).

Alternatively, a patient may have indicated that particular information is sensitive information and that the patient may wish to conceal this information ("Yes" branch STEP 1003). In this case, the system optionally determines if the data is essential or non-essential (STEP 1004). If the data is indicated as sensitive information (e.g., by the patient) and non-essential (STEP 1004) and/or capable of being summarized, the data may be summarized (STEP 1006). Thus, information may be concealed while maintaining diagnostic and therapeutic effectiveness.

As an example to illustrate, data of a patient may include ECG information which may also include abnormal rhythm patterns or other anomalies indicating various cardiac pathologies. The patient may desire to keep certain portions of the information private while may agree to provide other portions of the information. The patient may further indicate preferences in a profile and may provide the profile to the system. Based on preferences of the patient, the information deemed non-sensitive may be included in the transmission to the health care provider and may further be shared with other relevant parties, if desired. Sensitive portions of the patient data (e.g., specific arrhythmias detected or other sensitive information) may be concealed and may not be transmitted to the health care provider or other parties without further authorization from the patient. In another example, the concealed data (i.e., data deemed to be sensitive information) may be provided to the health care provider or other relevant party in an alternate form. For example, the data may be summarized and provided in summary form rather than in detailed form. In this example, the ECG information deemed sensitive may be summarized such that the patient data transmission to the health care provider may indicate that the an anomaly exists in the data. However, the specific anomaly is not provided in the transmission. In this way, the health care provider may be alerted to a potentially abnormal value in the patient data while maintaining privacy issues of the patient. Thus, the preferences of the patient may be provided in preference tools and/or controls to allow patients to share multiple streams of data containing information the patient may desire to share while keeping more sensitive information private. In one example, raw data corresponding to the patient data may be converted into composite information (i.e., a less-sensitive format) while still providing sufficient information to the healthcare provider.

The healthcare provider may also access the sensitive information subsequently, for example, by special permission. In this example, the healthcare provider may indicate the desire to collect previous ECG readings from the patient over a specified period of time. Hence, the healthcare provider may input a request to a central component to access the information from the sensor devices of the patient. The central component may verify the healthcare provider as authorized to access the information (e.g., password or other security means) and may provide the data to the healthcare provider as requested. In this way, the healthcare provider may identify suspicious findings in the screened non-sensitive information including summaries of the patient data and may further obtain more detailed information corresponding to the suspicious portions of the data after authentication by the system.

In this example, real-time dialog capabilities may be provided to a patient and healthcare provider. The healthcare provider may communicate with the patient or with a central component to obtain information regarding the patient. For example, patient data may be provided by sensor devices of the patient to a central component. Based on a patient profile of preferences or controls, a portion of the patient data may be deemed sensitive while another portion of the data may not be deemed sensitive. The information not deemed to be sensitive may be transmitted to the healthcare provider while the information deemed to be sensitive may be transmitted to the healthcare provider in a different form. For example, the sensitive information may be summarized or abstracted to provide information to the healthcare provider that an abnormality may exist. Thus, details of the sensitive information may be withheld initially to preserve privacy. The healthcare provider may also access the detailed sensitive information as described after an authentication procedure. For example, the healthcare provider may engage in a dialog with either the central component or the patient which may include identification of the healthcare provider or authentication of the healthcare provider. The healthcare provider may thus receive access to sensitive information corresponding to the patient outside of the usually privacy policy of the patient.

In another example, sensitivity levels of information deemed to be sensitive by a patient may be overridden by the system if the information is considered essential ("Yes" branch of STEP 1004). In this example, the patient may indicate that a certain portion of information is sensitive and indicate that the data should not be transmitted in its original form (i.e., detailed information should not be transmitted).

However, it may be determined that the information is essential information in which the healthcare provider may need the information to formulate a proper diagnosis or treatment plan. For example, such parameters may be stored in memory and may be accessed by the system to determine if the information is necessary or highly desired by a healthcare provider. If the information is deemed essential in that the information is highly desired by the healthcare provider or would be considered important to a healthcare provider, then the system may transmit detailed information to the healthcare provider (STEP 1005). Alternatively, the system may query the patient to indicate that the information is deemed sensitive but that the information is also deemed essential. The patient may have an option to choose if the information may be sent to the healthcare provider or not.

Information collected from sensor devices may also be analyzed for accuracy, reliability or errors. For example, sensed data may be received from a plurality of sensor devices. Each of the sensor devices may provide similar or related data. For example, one sensor device may provide oxygen saturation values from arterial blood gas analysis while another sensor device may provide oxygen saturation values from a pulse oximeter. In another example, a first sensor device may be an ECG device that may provide a tracing indicating a heart rate while a second device may be a pulse monitor that may also provide a heart rate. In addition, any number of sensor devices may provide additional oxygen saturation values or heart rate data in these examples.

Alternatively, different sensor devices may provide different but related data points such that one returned value from one sensor device may confirm a returned value from another sensor device. For example, a blood pressure monitor may provide a low blood pressure reading while a heart rate monitor may indicate tachycardia or a rapid heart rate. In this example, one sensor device may confirm reliability or accuracy of a second sensor device.

Hence, a group of sensor device may provide similar or related data such that the reliability or accuracy of each of the devices may be ascertained. If one device in the group of sensor devices provides erroneous or inaccurate readings, then the erroneous sensor device may be identified based on the readings from the other sensor devices in the group. Identification of the erroneous sensor device may be accomplished by assigning a reliability factor to the sensor device and the corresponding medical data based on comparing the medical data with medical data from other sensor devices. For example, medical data of a corresponding type may be received from plurality of devices and compared. Medical data from one device may be identified as substantially different from corresponding medical data from other devices and may be assigned a reliability factor indicating potentially erroneous data based on the identification. Different reliability factors may be assigned to different devices or corresponding received medical data based on the analysis. Each of the medical data may be transported to a healthcare provider with a corresponding reliability factor. The reliability factors may thus inform the healthcare provider as to reliability of the medical data being received by respective devices.

In one example, a group of values for a parameter may be received at a central component that may describe a similar patient data feature. The central component may compare the data and may determine an outlying value from a particular sensor device. The identified sensor device may be thus be identified as unreliable. In another example, the sensed data from the different sensor devices in the group of devices may be sent to a healthcare provider with a reliability indicator. The reliability indicator may indicate the accuracy, reliability or likelihood of accuracy of the data for each corresponding sensor devices. In this example, data from sensor devices providing values that differ from a predetermined number of devices in the group of sensor devices by a predetermined amount may be identified as unreliable. A message or other type of indicator may be transmitted to the healthcare provider to inform the healthcare provider that the identified sensor device is not reliability. This indicator may accompany the sensed data transmitted from each of the devices.

In another example, a computer-readable medium having computer-executable instructions stored thereon is provided in which execution of the computer-executable instructions performs a method as described above. The computer-readable medium may be included in a system or computer and may include, for example, a hard disk, a magnetic disk, an optical disk, a CD-ROM, etc. A computer-readable medium may also include any type of computer-readable storage media that can store data that is accessible by computer such as random access memories (RAMs), read only memories (ROMs), and the like.

It is understood that aspects of the present invention can take many forms and embodiments. The embodiments shown herein are intended to illustrate rather than to limit the invention, it being appreciated that variations may be made without departing from the spirit of the scope of the invention. Although illustrative embodiments of the invention have been shown and described, a wide range of modification, change and substitution is intended in the foregoing disclosure and in some instances some features of the present invention may be employed without a corresponding use of the other features. Accordingly, it is appropriate that the appended claims be construed broadly and in a manner consistent with the scope of the invention.

The invention claimed is:

1. A method for providing data from a network of sensors sensing medical data, the method comprising:
   receiving medical data from the sensors;
   generating a priority value for the received medical data including:
      determining a type of the received medical data;
      assigning a priority value to the received medical data based on the type;
      comparing the received medical data with an expected corresponding normal value; and
      assigning the priority value based on the comparing step including:
         assigning a first priority value to the received medical data if the received medical data is within an expected range of normal values, otherwise assigning a second priority value, the second priority value being higher than the first priority value;
         assigning the second priority value to the received medical data if the received medical data is outside the expected range of normal values but within a predetermined range of values, otherwise assigning a third party priority value, the third priority value being higher that the second priority value;
   transporting the medical data to a healthcare provider according to the priority values; and
   comparing the priority value of the received medical data to the priority values of other received medical data and transporting the received medical data to the healthcare provider if the priority value of the received medical data is greater than or equal to the priority values of the other received medical data, wherein the priority value of at least one other received medical data is greater than the priority value of the received medical data, the method further comprising transporting the at least one other received medical data substantially simultaneously with the received medical data and wherein the at least one other received medical data is transported with an indicator, the indicator indicating that the at least one other received medical data has priority.

2. The method of claim 1 wherein the predetermined range of values comprises values within a predetermined percentage of the expected range of normal values.

3. The method of claim 1 wherein the step of assigning the priority value based on the comparing step includes assigning the third priority value to the received medical data and the step of transporting includes transporting the received medical data to an emergency service based on the assigning.

4. The method of claim 1 further comprising transporting other received medical data having a priority value greater than the received medical data prior to transporting the received medical data to the healthcare provider.

5. The method of claim 1 wherein the indicator includes a position in a list.

6. The method of claim 1 further comprising:
sorting the received medical data and the other received medical data based on corresponding priority values; and
generating a list of medical data in order of priority values,
wherein the step of transporting includes transporting the list of medical data to the healthcare provider.

7. The method of claim 1 wherein the step of assigning the priority value based on the comparing step includes:
assigning the first priority value to the received medical data; and
comparing the priority value of the received medical data to the priority values of other received medical data and transporting the received medical data to the healthcare provider if the priority value of the received medical data is greater than or equal to the priority values of the other received medical data.

8. The method of claim 7 further comprising transporting other received medical data having a priority value greater than the received medical data prior to transporting the received medical data to the healthcare provider.

9. The method of claim 7 further comprising batching the received medical data with other medical data having a priority value about equal to the first priority value.

10. The method of claim 1 wherein the step of transporting includes filtering the medical data based on the priority value, wherein the filtered medical data is not transported to the healthcare provider.

11. The method of claim 1 further comprising:
comparing the received medical data with previously received medical data corresponding to a subject; and
assigning a relevance value to the received medical data based on the comparing step,
wherein generating the priority value includes generating the priority value based on the relevance value.

12. The method of claim 11 wherein the comparing includes identifying a difference between the received medical data and the previously received medical data, the identified difference including a trend associated with a change of the received medical data from the previously received medical data.

13. The method of claim 12 wherein the trend indicates pathophysiology of the subject.

14. The method of claim 12 wherein the trend includes one of an increase or a decrease of a value corresponding to the received medical data, the trend corresponding to a likelihood of pathophysiology in the subject.

15. The method of claim 14 further comprising measuring the trend over a period of time, wherein generating the priority value further includes generating the priority value based on the trend over the period of time.

16. A method for providing data from a network of sensors sensing medical data, the method comprising:
receiving medical data from the sensors;
generating a priority value for the received medical data; and transporting the medical data to a healthcare provider according to the priority values;
receiving input from a subject, the input comprising a preference for data privacy;
identifying at least a portion of the received medical data as private based on the preference; and
filtering the identified at least a portion of the received data,
wherein the transporting includes transporting a portion of the received medical data not filtered.

17. The method of claim 16 wherein filtering includes summarizing the filtered identified data and wherein the transporting further includes transporting the summarized filtered identified data.

18. The method of claim 17 wherein filtering includes forming a composite of the identified at least a portion of the received data and wherein the transporting further includes transporting the composite data.

19. The method of claim 16 further comprising:
receiving input from a healthcare provider, the input including a request for access to the identified at least a portion of the received data;
transporting the identified at least a portion of the received data based on the request.

20. The method of claim 19 wherein the input includes an authenticator for verifying the healthcare provider.

21. A method for identifying healthcare data sensors in a sensor device network, the method comprising:
receiving medical data from a plurality of sensor devices;
identifying a type of medical data from each of the sensor devices in the plurality of sensor devices;
comparing matching types of medical data from each corresponding sensor device in the plurality of sensor devices;
assigning a reliability factor to sensor devices based on the comparing; transporting the medical data including the assigned reliability factor,
wherein the comparing includes identifying a first sensor device in the plurality of sensor devices, wherein the first sensor device provides medical data that is substantially different from the medical data from each corresponding sensor device in the plurality of sensor devices and wherein the assigning comprises assigning a first reliability factor to the first sensor device and a second reliability factor to each corresponding sensor device in the plurality of sensor devices, wherein the first reliability factor is different from the second reliability factor.

22. The method of claim 21 wherein the first reliability factor indicates a predicted accuracy level of the medical data from the first sensor device.

* * * * *